(12) United States Patent
Gharib et al.

(10) Patent No.: US 7,998,190 B2
(45) Date of Patent: Aug. 16, 2011

(54) INTRAVASCULAR MINIATURE STENT PUMP

(75) Inventors: Morteza Gharib, San Marino, CA (US);
Anna Iwaniec, Sierra Madre, CA (US);
Richmond A. Wolf, Pasadena, CA (US)

(73) Assignee: California Institute of Technology,
Pasadena, CA (US)

( * ) Notice: Subject to any disclaimer, the term of this patent is extended or adjusted under 35 U.S.C. 154(b) by 23 days.

(21) Appl. No.: 10/420,170

(22) Filed: Apr. 21, 2003

(65) Prior Publication Data

US 2003/0233143 A1    Dec. 18, 2003

Related U.S. Application Data

(60) Provisional application No. 60/389,176, filed on Jun. 17, 2002.

(51) Int. Cl.
*A61M 1/12* (2006.01)
*A61F 2/90* (2006.01)

(52) U.S. Cl. ............................ 623/1.15; 623/3.13; 604/9
(58) Field of Classification Search ........ 623/3.13–3.15, 623/3.1–3.12, 3.16–3.26; 604/9
See application file for complete search history.

(56) References Cited

U.S. PATENT DOCUMENTS

| | | | |
|---|---|---|---|
| 5,147,388 A * | 9/1992 | Yamazaki | 623/3.13 |
| 5,643,207 A | 7/1997 | Rise | |
| 5,735,897 A | 4/1998 | Buirge | |
| 5,746,709 A | 5/1998 | Rom et al. | |
| 5,759,017 A | 6/1998 | Patton et al. | |
| 5,820,589 A | 10/1998 | Torgerson et al. | |
| 5,840,069 A | 11/1998 | Robinson | |
| 6,136,025 A | 10/2000 | Barbut et al. | |
| 6,143,035 A * | 11/2000 | McDowell | 623/22.11 |
| 6,210,318 B1 | 4/2001 | Lederman | |
| 6,254,355 B1 | 7/2001 | Gharib | |
| 6,436,091 B1 | 8/2002 | Harper et al. | |
| 6,468,200 B1 | 10/2002 | Fischi | |
| 6,506,025 B1 | 1/2003 | Gharib | |
| 6,508,787 B2 | 1/2003 | Widmann et al. | |

FOREIGN PATENT DOCUMENTS

| | | |
|---|---|---|
| JP | 8-19600 A * | 1/1996 |
| JP | 2001-112796 A * | 4/2001 |
| WO | WO 97/41799 A1 * | 11/1997 |
| WO | WO 00/35515 A1 * | 6/2000 |
| WO | WO 00/62838 A2 * | 10/2000 |

* cited by examiner

*Primary Examiner* — David H. Willse
(74) *Attorney, Agent, or Firm* — Law Office of Scott C. Harris, Inc.

(57) ABSTRACT

An intravascular miniature stent pump comprising an intravascular stent for implantation at an implant site within a blood vessel and a miniature pump mounted on the stent, wherein the pump allows an adequate blood flow to prevent clotting within a lumen of the stent, and wherein the blood flow is equal to or greater than a blood flow at the implant site before implantation.

43 Claims, 5 Drawing Sheets

INTRAVASCULAR MINIATURE STENT PUMP

CROSS-REFERENCE TO RELATED APPLICATION

The present application claims the benefit of provisional application Ser. No. 60/389,176, filed Jun. 17, 2002; the entire contents of which are incorporated herein by reference.

FIELD OF THE INVENTION

The present invention generally relates to a fluid pumping system within a stent. More particularly, the present invention relates to the intravascular stent pump incorporating a bladeless pump embedded in a cardiovascular stent for enhancing dysfunctional lower body circulation, increased venous return, or coronary perfusion.

BACKGROUND OF THE INVENTION

A stent is made of a plastic or metallic material in the form of a cylindrical mesh that is inserted into a vein or artery in order to maintain the cross-sectional area of the blood vessel. A conventional stent generally expands beyond the size of a healthy blood vessel to help compensate or increase the blood flow. It is desirable to keep the flow velocity within the length of the stent at above a threshold number to prevent clotting.

Many different pump systems are known, for example, impeller pumps, gear pumps, piston pumps, vacuum pumps and the like. A typical pump uses an impeller or a set of blades, which spins to push a flow of fluid in one direction. Less conventional pump designs without impellers are also known, such as peristaltic pumps, magnetic flux pumps, electroosmotic micropumps, or diaphragm pumps that are used in places where the fluid can actually be damaged or the setup space is sufficient. In a cardiovascular application, special features for pumping of red blood cells that avoid damaging the red blood cells are mandatory in a stent pump system.

U.S. Pat. No. 6,136,025 issued on Oct. 24, 2000, the entire contents of which are incorporated herein by reference, discloses a method of inserting a stent having a pump mounted in an anterior of the stent to a peripheral artery or vein, expanding the stent in place, and activating the pump to increase blood flow downstream of the pump. The pump would occupy only a fraction of the stent lumen when expanded, wherein a helical type pump is employed.

U.S. Pat. No. 5,840,069 issued on Nov. 24, 1998, the entire contents of which are incorporated herein by reference, discloses an implantable peristaltic pump having a first race supports the tube in a plane, roller means for compressing the tube at one or more points along the path in a direction non-parallel to the plane, and means for moving the roller means relative to the tube along the path so that liquid is moved through the tube.

U.S. Pat. No. 6,210,318 issued on Apr. 3, 2001, the entire contents of which are incorporated herein by reference, discloses a stented balloon pump system configured to be positioned within a desired body passageway, the balloon pump being unconnected to and separately positionable with respect to the stent, wherein the stent substantially reduces compliance of the body passageway, thereby improving the efficiency of the fluid pumping therethrough.

U.S. Pat. No. 5,735,987 issued on Apr. 7, 1998, the entire contents of which are incorporated herein by reference, discloses an intravascular stent pump constructed and arranged in a laminate structure to release therapeutics into the blood stream.

U.S. Pat. No. 6,254,355 to Morteza Gharib, one of co-inventors of the present invention, the entire contents of which are incorporated herein by reference, discloses a valveless fluid system based on pinch-off actuation of an elastic tube channel at a location situated asymmetrically with respect to its two ends. Means of pinch-off actuation can be either electromagnetic, pneumatic, mechanical, or the like. A critical condition for the operation of the "hydroelastic pump" therein is in having the elastic tube attached to other segments that have a different compliance (such as elasticity). This difference in the elastic properties facilitates elastic wave reflection in terms of local or global dynamic change of the tube's cross-section which results in the establishment of a pressure difference across the actuator and thus unidirectional movement of fluid. The intensity and direction of this flow depends on the frequency, duty cycle, and elastic properties of the tube.

U.S. Pat. No. 6,506,025 to Morteza Gharib, one of co-inventors of the present invention, the entire contents of which are incorporated herein by reference, discloses a bladeless pump which uses a rotating impeller to produce a fluid flow in a direction substantially perpendicular to the direction of rotation. An electric motor or other rotation driving source can provide rotational force to the end of the impeller.

None of the above-cited prior art discloses an intravascular miniature stent pump suitably for maintaining the flow velocity within the stent at above the threshold for blood clotting. Therefore, it is one aspect of the present invention to provide an intravascular miniature stent pump comprising an intravascular stent for implantation in a lesion site and a miniature pump mounted on the stent, wherein the stent pump allows adequate blood flow suitable in blood perfusion.

SUMMARY OF THE INVENTION

It is one object of the present invention to provide an intravascular miniature stent pump comprising an intravascular stent for implantation at an implant site within a blood vessel, and a miniature pump mounted on or embedded in the stent, wherein the pump allows an adequate blood flow to prevent clotting within a lumen of the stent.

It is another object of the present invention to provide an intravascular miniature stent pump system for a blood vessel comprising an intravascular stent, a bladeless pump mounted on the stent, the bladeless pump comprising an inner element, which is rotatably mounted to rotate around a rotation axis, and which has a substantially smooth outer surface which has a substantially constant and continuous outer diameter cylindrical surface, and a chamber surface, wherein the chamber surface surrounds the inner element and has an inlet of fluid, at a first location along the rotation axis and an outlet for transmitting pumped fluid, at a different location along the rotation axis.

It is still another object of the present invention to provide an intravascular miniature stent pump system for a blood vessel comprising an intravascular stent and a bladeless pump mounted on the stent, the bladeless pump comprising a rotating part, which has no blades or grooves thereon and which rotates to produce a fluid flow in a direction substantially perpendicular to a direction of rotation.

It is a further object of the present invention to provide a method for pumping fluid in a vessel of a human body, the method comprising positioning an endoluminal miniature stent pump at a desired site of the vessel, wherein the stent pump comprises a stent and a miniature pump mounted on the stent, and pumping fluid by activating the miniature pump. In one embodiment, the miniature pump is mounted within a lumen of the stent, wherein the pump allows an adequate fluid flow within the lumen of the stent.

BRIEF DESCRIPTION OF THE DRAWINGS

Further features and advantages of the present invention will become apparent to one of skill in the art in view of the Detailed Description of Exemplary Embodiments that follows, when considered together with the attached drawings and claims.

DETAILED DESCRIPTION OF EXEMPLARY EMBODIMENTS

Figure 1:
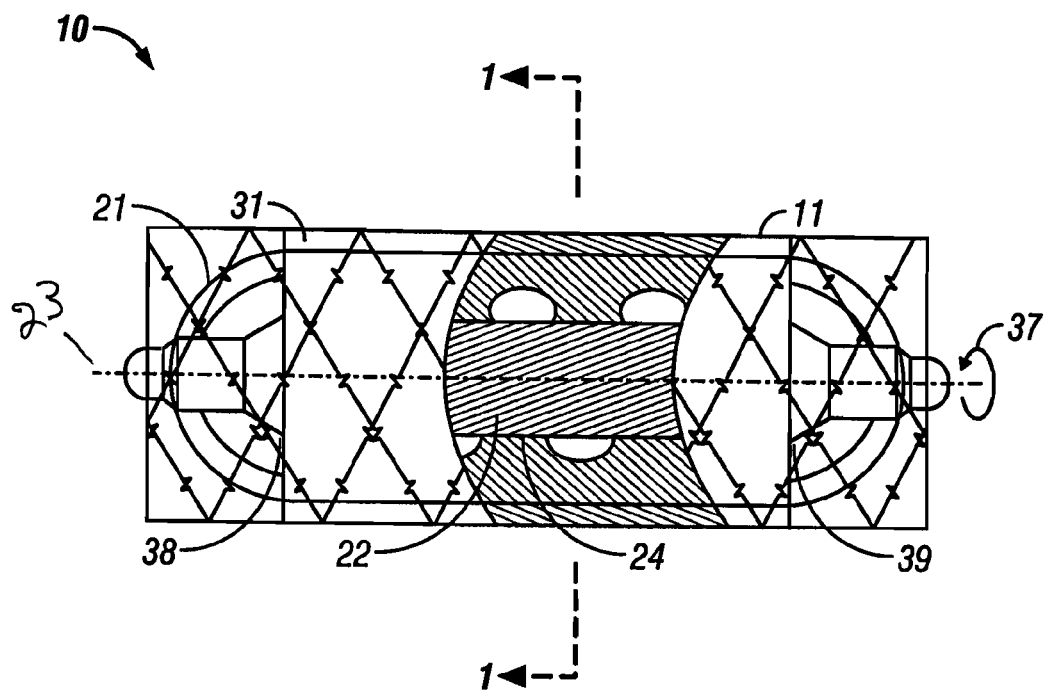
FIG. 1 is a first embodiment of the stent pump according to the principles of the present invention.

The preferred embodiments of the present invention described below relate particularly to an intravascular miniature stent pump that can be implanted using a catheter, a cannula or surgically. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described below.

While current stent technology is the best-known treatment for atherosclerosis, the intravascular miniature stent pump (IMSP) can improve upon the performance in several ways. The IMSP system sustains a continuous flow of blood without the need for a large diameter stent. The IMSP system compensates for blood perfusion by increasing blood flow through added momentum rather than increasing the cross-sectional area of the blood vessel. Because the cross-sectional area is maintained, there is no need to perturb deposited plaques that could cause further complications. The IMSP system maintains unidirectional flow that can prevent clotting. The stent pump would provide blood perfusion during the entire cardiac cycle.

To meet a variety of medical applications, the pump element of the IMSP system may be selected from the group consisting of turbine pumps, bladeless turbine pumps, peristaltic pumps, impedance pumps, impeller pumps, gear pumps, piston pumps, vacuum pumps, magnetic flux pumps, electroosmotic micropumps, hydroelastic pumps, diaphragm pumps, and the like. The non-mechanical electroosmotic pump uses electroosmotic flow in a porous media to generate pressures in excess of 10 and even 100 atms. The pressure capacity of an electroosmotic pump far exceeds the capacity of the other reported micropumps, which have a limit of 1 atm. This pump design has the advantage of being compatible with aqueous solutions as working fluid and is beneficial to be coupled to a stent as an endoluminal miniature stent pump in some medical applications.

The intravascular miniature stent pump is a combination of current stent technology and a miniature or nano pump integrated with the stent by embedding it inside or mounted adjacent to the stent. In one aspect, the stent pump system is to allow a blood flow equal to or greater than the blood flow at the implant site before the stent pump implantation. In another aspect, the stent pump system is to increase the downstream flow of the pump for enhanced perfusion or increased venous return. In still another aspect, the stent pump operates to temporarily counter or decrease the normal blood flow so as to maintain a decreased downstream flow for the body to recover or heal naturally, such as would be useful in an acute stroke patient. In a further aspect, the stent pump is to maintain a forward flow and a backward flow capabilities, in combination, suitably enabling perfusion enhancement for a patient or enabling reduced flow when stroke is indicated. In some aspect of the invention, it is provided a stent pump that either enhance, reduce, or reverse the forward flow downstream of the pump so as to maximize the therapeutic effects of the blood flow variations to a patient.

For arterial vessel placement, the system can be attached to the end of a catheter and delivered percutaneously through a femoral artery, a carotid artery, a left subclavian artery, and the like. For venous vessel placement, the system can be delivered through an iliac vein, a jugular vein, a femoral vein, subclavian vein, and the like. Typically a stent pump of approximately 1 to 10 mm in diameter, preferably 2 to 4 mm in diameter, is desirable depending on the location and the need for perfusion. The term "miniature" is herein intended to mean the stent pump size is relative small suitable for implantation with acceptable functions. In some aspects of the present invention, the stent pump system herein includes an intravascular miniature stent pump, an endoluminal miniature stent pump, an intravascular stent pump or an endoluminal stent pump.

The pump can be active as it is being delivered endoluminally so as to prevent blood clotting during the procedures, either percutaneously, minimally invasively or surgically. The intravascular miniature stent pump is mostly applicable to be implanted at an implant site of a blood vessel selected from a group consisting of an artery, a coronary artery, a periphery artery, a vein, a vena cava, a vein with chronic venous insufficiency, a vein with dysfunctional venous valve, and the like.

The stent can be made of a plastic or metal material in the form of a cylindrical mesh that is inserted into a vein or an artery in order to maintain the blood vessel's cross-sectional area. Traditional stents expand beyond the size of a healthy blood vessel to help increase the blood flow. With the addition of a bladeless rotary pump or other suitable pump for maintaining suitable blood flow, it is unnecessary to over-enlarge the vessel diameter. The stent element of the stent pump would be for minimal structural support as well as to provide an attachment mechanism. In some aspects of the present invention, it is provided an endoluminal stent pump comprising a functional pump secured to a stent-type supporting structure.

FIG. 1 shows a first preferred embodiment of the stent pump prior to expansion according to the principles of the present invention. An intravascular miniature stent pump system 10 for a blood vessel comprises a stent element 11 and a pump element 21 mounted on the stent 11. The bladeless pump element 21 comprises an inner element 22, which is rotatably mounted to rotate around a rotation axis 23 (as shown by an arrow 37), and which has a substantially smooth outer surface 24 which has a substantially constant and continuous outer diameter cylindrical surface. The system further comprises a chamber surface, wherein the chamber surface surrounds the inner element 22 and has an inlet of fluid, at a first location 38 along the rotation axis 23 and an outlet for transmitting pumped fluid, at a different location 39 along the rotation axis 23.

In one alternate embodiment, the inner element 22 rotates in a revered direction as opposite to the one shown by the arrow 37, wherein the second location 39 becomes the inlet of fluid and the first location becomes the outlet of fluid. Therefore, the same stent pump can be used to pump fluid in one direction or in an opposite direction according to the needs by controlling the rotation of the inner element 22 either clockwise or counter-clockwise around the rotation axis 23.

U.S. Pat. No. 6,506,025 to Morteza Gharib, one of co-inventors of the present invention, the entire contents of which are incorporated herein by reference, discloses a bladeless pump which uses a rotating impeller to produce a fluid flow in a direction substantially perpendicular to the direction of rotation. An electric motor or other rotation driving source can provide rotational force to the end of the impeller. It is one aspect of the present invention to provide an intravascular miniature stent pump system for a blood vessel, the system comprising an intravascular stent and a bladeless pump mounted on the stent, the bladeless pump comprising a rotating part, which has no blades or grooves thereon and which rotates to produce a fluid flow in a direction substantially perpendicular to a direction of rotation.

Figure 2:
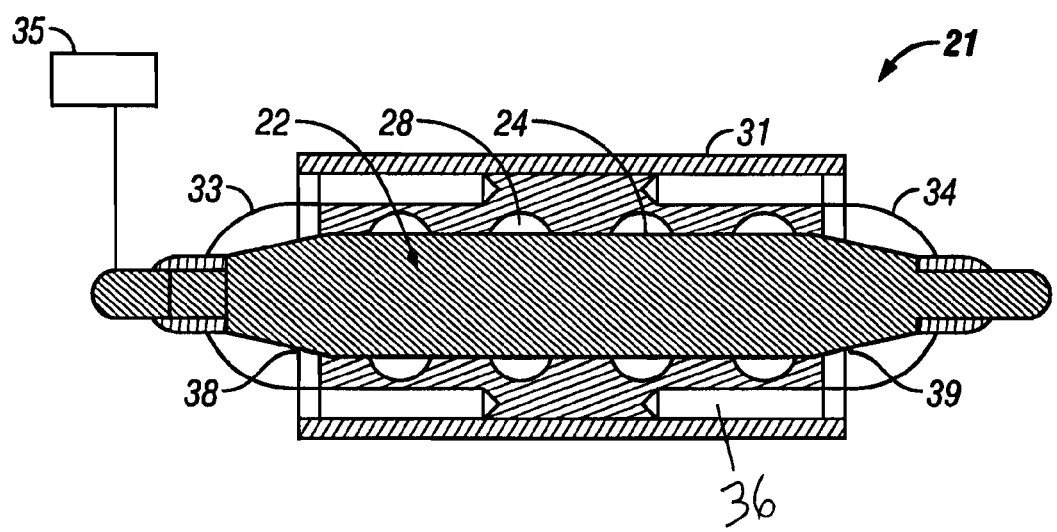
FIG. 2 is a front cross-sectional view of the pump element of the stent pump in FIG. 1.
Figure 3:
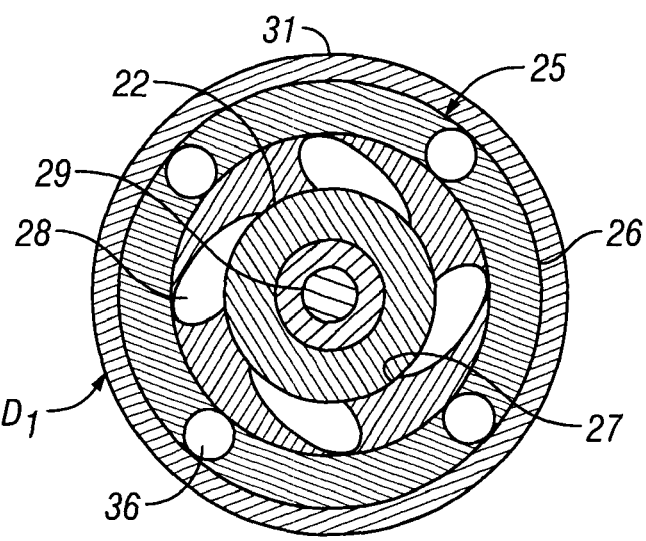
FIG. 3 is a side cross-sectional view of the stent pump, section 1-1 of FIG. 1.

In one preferred embodiment, FIG. 2 shows a bladeless pump component or element 21 of the stent pump 10 while FIG. 3 shows a side cross-sectional view of the stent pump 10, section 1-1 of FIG. 1. The pump 21 is surrounded and securely covered by a cylindrical balloon wrap 31 that is collapsibly expandable, wherein the outer periphery of the balloon wrap is properly secured to the inner surface of the stent component or element 11. The endoluminal stent construct, material and manufacturing methods have been disclosed in prior art and well known to an ordinary artisan skilled in that art. In procedures, when the stent element 11 expands, the balloon wrap 31 may also expand and enable the intravascular stent 11 to be adapted to fit the implant site. In one aspect of the invention, the miniature or nano pump 21 is suitably configured and mounted at an appropriate position within the lumen of the stent enabling pumping adequate blood flow through the lumen of the stent element 11 to prevent clotting therein.

As illustrated in FIGS. 2 and 3, the pump element 21 is formed of two coaxial cylinders, one rotating within the other. An outer cylindrical housing 25 includes an outer surface 26 which can be of any desired size or shape. The pump element is held together and supported by a plurality of housing supports 36. In one embodiment, the inner surface 27 of the outer housing 25 is formed with spirally-patterned grooves 28 thereon. The central axis 29 of the outer housing 25 defines a direction of fluid pumping.

Further, a fluid pumping element 22 is located coaxially with the central axis 29. The fluid pumping element 22 has a substantially smooth outer surface 24. It preferably has no blades thereon. Blades, as that term is used herein, are sharp edged objects, such as the usual fan-shaped parts that are used in a pump. In one embodiment, the fluid pumping element 22 is cylindrical and has a substantially constant outer diameter over its entire active surface. That constant outer diameter can be essentially constant within 1 to 5 percent. The fluid pumping element can be a solid element, or can be a hollow element, such as a tube. In the case of a hollow element, the blood flow can be maintained essentially constant through the lumen of the hollow element regardless of the pumping action. The pumping shaft is held rotatably at its two ends by a first shaft holder 33 and a second shaft holder 34. The shaft can rotate within the first and second shaft holders. An electric motor 35 or other powered rotating means can provide rotational force to the end of the shaft.

In some aspect of the invention, it is provided a pump that is electrically connected to a motor, wherein the pump could be powered telemetrically or by an implantable battery. The pump may alternately be powered by electricity that is converted from body heat based on Peltier effects, or powered by electricity that is converted from mechanical motion of muscles based on piezoelectric mechanism. The material or the outer surface of the motor or electrical wires are made of biocompatible material or coated with biocompatible agents. In one embodiment, the stent or the pump elements may be loaded with slow-releasing drugs as a drug-eluting stent pump. The power sources for a pump and conversion of mechanical energy to electrical energy are well known to one skilled in the art.

In one embodiment, the bladeless rotary pump 21 is an axial flow pump design that comprises of a smooth inner shaft and an outer cylindrical chassis with helical grooves carved from the inner surface. The inner shaft is rotated inside the chassis using a motor that may be connected externally or embedded within the device. The friction of the shaft against the blood causes it to flow while the grooves in the chassis channel the fluid unidirectionally. Depending on the exact geometry chosen for the shaft and the chassis and the rotational velocity of the shaft, the flow rate can be adjusted between 0.01 to 1 liters per minute, preferably between about 0.1 to 0.3 liters per minute.

In certain embodiments of the pump, a wire, having proximal and distal ends, may be connected to the pump at the distal end and a battery at the proximal end. The battery is placed subcutaneously and powered telemetrically, thereby reducing the risk of infection associated with placement of the battery outside a patient's body. The design and construction of telemetrically-powered batteries is well-known to those having ordinary skill in the art. Alternatively, the battery is placed at the core of the pump. In certain embodiments, two or more batteries or pumps are placed in sequence to allow for separate recharging. Anticoagulants, such as heparin and heparinoids, may be applied to the stent pump to reduce the chances of blood clotting. Anticoagulants may include heparinoids, hirudin, monoclonal antibodies, or the like. The anticoagulant may be painted or sprayed onto the pump and/or the stent. A chemical dip comprising the anticoagulant also may be used. Other methods known in the art for applying chemicals to a stent pump may be used. Systemic anticoagulation may or may not be required.

Figure 4:
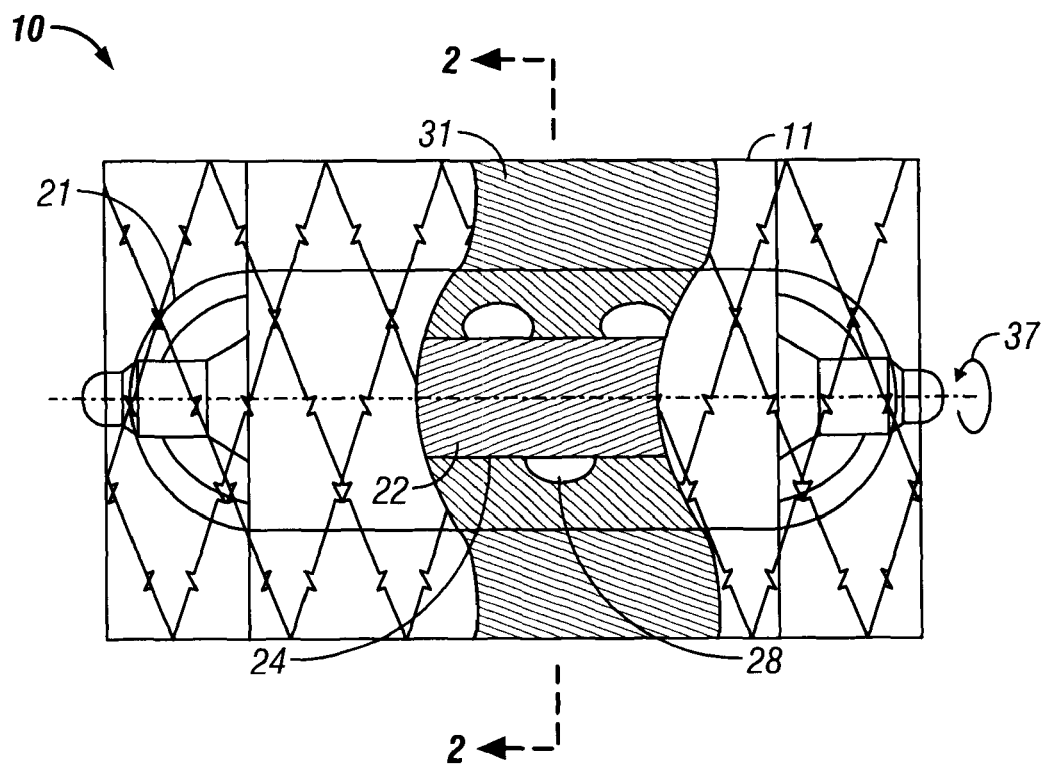
FIG. 4 is a second embodiment of the stent pump of FIG. 1 after expansion according to the principles of the present invention.
Figure 5:
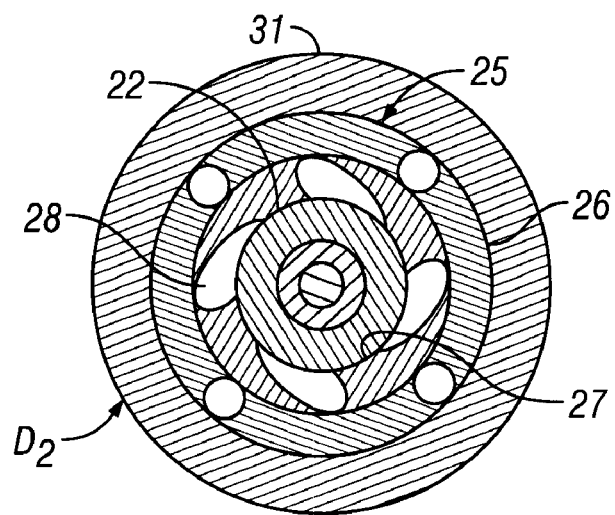
FIG. 5 is a cross-sectional view of the stent pump, section 2-2 of FIG. 4.

FIG. 4 shows a second embodiment of the stent pump 10 of FIG. 1 after expansion according to the principles of the present invention, while FIG. 5 shows a cross-sectional view of the stent pump, section 2-2 of FIG. 4. In operations, after delivering the stent pump 10 to an implant site of a vessel, the stent element 11 is suitably expanded and adapted to be expanded to fit the implant site. In one embodiment, the built-in balloon wrap 31 is expanded by injecting an inflatable fluid into cavity of the balloon wrap 31 so as to expand the stent element 11. The balloon wrap 31 covers and secures to at least a portion of the outer surface 26 of the outer cylindrical housing 25. For illustration, the balloon wrap 31 has a balloon thickness $D_1$ before expansion and a thickness $D_2$ after expansion, wherein $D_2$ is substantially greater than $D_1$. In another embodiment, the stent element 11 is made of a collapsibly expandable material that is self-expanding. Therefore, it is provided an intravascular stent balloon expandable or self-expanding. At least a portion of the intravascular stent element 11 or the pump element 21 is made of a material selected from a group consisting of Nitinol, stainless steel, shape memory alloy, and biocompatible plastic.

In operations, a method for pumping fluid in a vessel of a human body comprises a) positioning an endoluminal miniature stent pump at a desired site of the vessel, wherein the stent pump comprises a stent and a miniature pump mounted on the stent, and b) pumping fluid by activating the miniature pump. In a preferred embodiment, the miniature pump is mounted within at least a lumen of the stent, and wherein the pump allows an adequate fluid flow within the lumen of the stent. The method further comprises the step of positioning the stent pump by providing a catheter having the stent pump releasably mounted on a distal end of the catheter, inserting the distal end of the catheter into the vessel, and advancing the catheter to position the stent pump at the desired site. A stent pump is also implantable in the body conduit, such as urethra, ureter and the like percutaneously.

U.S. Pat. No. 6,254,355 to Morteza Gharib, one of co-inventors of the present invention, the entire contents of which are incorporated herein by reference, discloses a valveless fluid system based on pinch-off actuation of an elastic tube channel at a location situated asymmetrically with respect to its two ends. The hydroelastic pump with means of pinch-off actuation may be mounted on a stent as an intravascular miniature stent pump. A critical condition for the operation of the "hydroelastic pump" therein is in having the elastic tube attached to other segments that have a different compliance (such as elasticity). This difference in the elastic properties facilitates elastic wave reflection in terms of local or global dynamic change of the tube's cross-section which results in the establishment of a pressure difference across the actuator and thus unidirectional movement of fluid. The design and construction of the hydroelastic pump as disclosed in U.S. Pat. No. 6,254,355 is well-known to those having ordinary skill in the art, the entire contents of which are incorporated herein by reference, and will not be further discussed herein.

U.S. Pat. No. 5,840,069 issued on Nov. 24, 1998 and U.S. Pat. No. 6,468,200 issued on Oct. 22, 2002 show an implantable peristaltic pump having roller means for compressing the tube at one or more points along the path, and means for moving the roller means relative to the tube along the path so that liquid is moved through the tube. The design and construction of peristaltic pumps are explained in numerous references well-known to those having ordinary skill in the art, all of which are incorporated herein by reference, and will not be further discussed herein.

Figure 6:
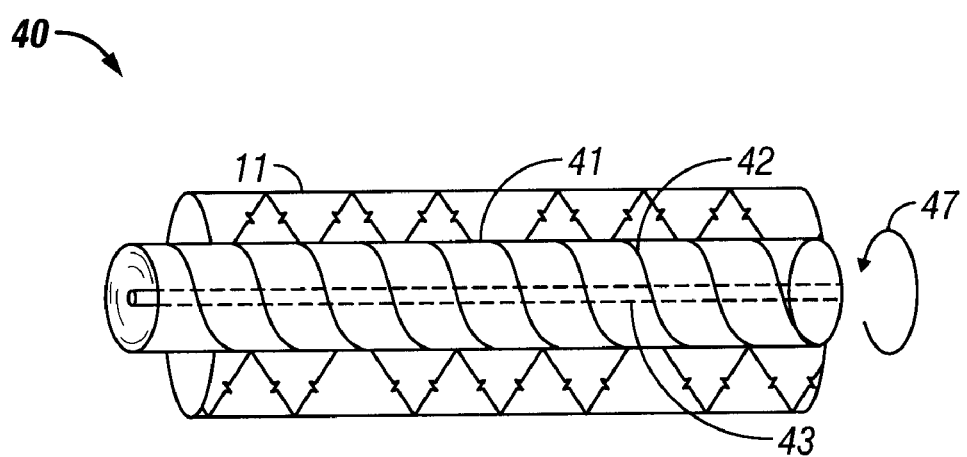
FIG. 6 is one embodiment of the stent pump comprising a helical pump.

FIG. 6 shows one embodiment of the stent pump 40 comprising a stent element 11 and a helical pump element 41 having a plurality of helical grooves or troughs 42. In one embodiment, the helical pump element 41 is powered to rotate (as shown in an arrow direction 47) by a lead screw 43 or other rotating driver. It is one object of the present invention to provide a stent pump comprising a pump securely mounted on a stent element, wherein the pump is selected from a group consisting of helical pumps, turbine pumps, bladeless turbine pumps, peristaltic pumps, impedance pumps, impeller pumps, gear pumps, piston pumps, vacuum pumps, magnetic flux pumps, electroosmotic micropumps, hydroelastic pumps, diaphragm pumps, and the like.

Figure 9:
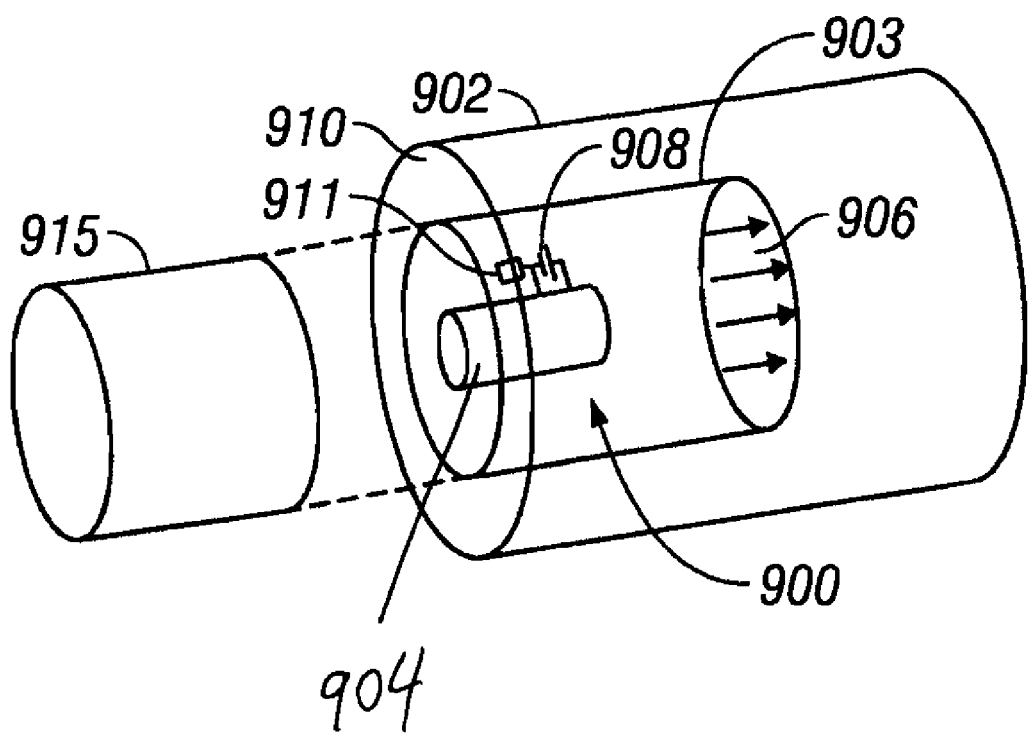
FIG. 9 shows an embodiment of a tube with a hydroelastic pump therein.

The stent pump could also be used as a lower body intravascular assist device as shown in FIG. 9, where the stent pump 900 is implanted into the interior portion 910 of a blood conduit 902 such as a vessel. The pump 900 may be attached to stent 903 as described herein. The pump includes the tube 904 as described herein, and may include a battery 908. A piezo mechanism 911 may be an alternative power source. The stent pump 900 is shown herein as a length of tubing, and it should be understood that this length of tubing can include a pump of the type illustrated in FIG. 1, or alternatively can be a hydroelastic pump, or a peristaltic pump. The device may be implanted via a catheter 915. There are several advantages to using the stent pump for preventing and treating symptoms, such as chronic venous insufficiency or enhanced perfusion through the arterioles and capillary beds. Further in another aspect, it is provided that the intravascular stent comprises a one-way valve 906 so as to maintain the fluid flow in one direction synchronized with the pump fluid direction and prevent fluid flow in an opposite direction.

Figure 7:
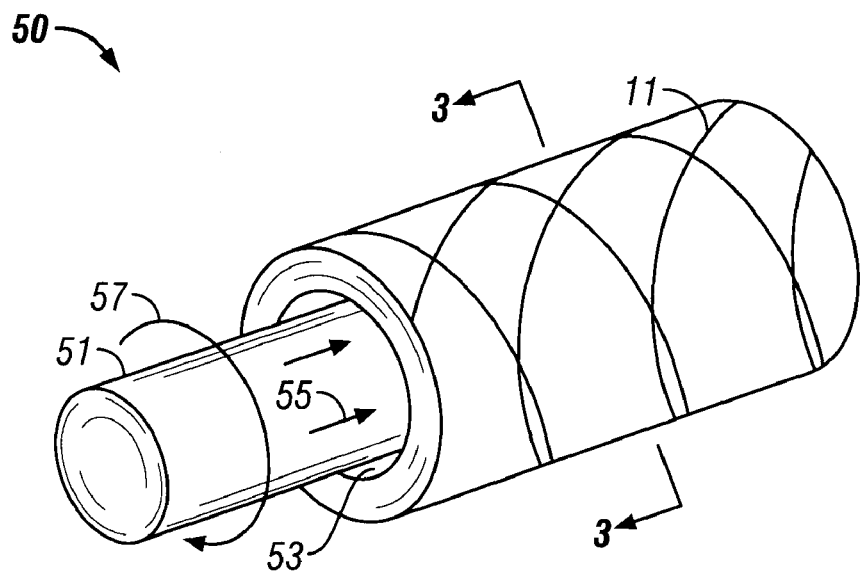
FIG. 7 is a perspective view of a stent pump comprising a helical pump.

FIG. 7 shows a perspective view of a stent pump 50 comprising a stent element 11 and a helical pump element or shaft 51, wherein the inner surface of the stent element 11 has a plurality of helical grooves or troughs 52. In one embodiment, the helical pump element 51 is powered to rotate (as shown by an arrow direction 57) and causes fluid to flow in clearance space 53 between the stent element 11 and the pump shaft 51 with a flow direction shown by an arrow 55.

Figure 8:
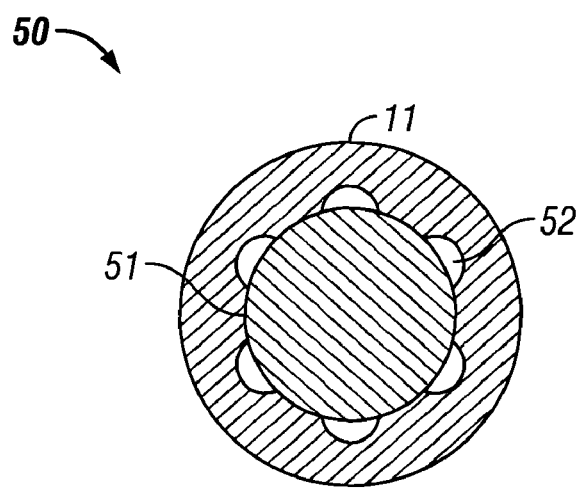
FIG. 8 is one embodiment of the helical stent pump, section 3-3 of FIG. 7.

FIG. 8 shows one embodiment of the helical stent pump 50, section 3-3 of FIG. 7. The plurality of helical grooves 52 is located on the inner surface of the outer stent element 11 as opposite to those helical grooves 42 located on the outer surface of the helical pump 41 (shown in FIG. 6). It is some aspect of the present invention to provide an intravascular miniature stent ump, comprising: an intravascular stent for implantation at an implant site within a blood vessel; and a miniature pump mounted on the stent, wherein the pump allows an adequate blood flow to prevent clotting within a lumen of the stent.

From the foregoing description, it will be appreciated that a novel intravascular miniature stent pump system and methods of use have been disclosed. While aspects of the invention have been described with reference to specific embodiments, the description is illustrative and is not intended to limit the scope of the invention. Various modifications and applications of the invention may occur to those who are skilled in the art, without departing from the true spirit or scope of the invention. The breadth and scope of the invention should be defined only in accordance with the appended claims and their equivalents.

What is claimed is:
1. An intravascular stent pump, comprising:
an intravascular stent for implantation at an implant site within a blood vessel wherein the intravascular stent comprises a one-way valve;
a pump mounted on said stent, wherein said pump assists with flow of blood within said blood vessel, said pump having a rotating part that contacts said blood within said blood vessel, and said rotating part being bladeless and having no grooves thereon, said rotating part being a cylinder with a cylindrical outer surface, and where the cylinder extends axially along a straight central axis and where said cylinder rotates around said axis during pumping, and wherein said cylinder has no grooves thereon and has no blades thereon and where the cylindrical surface contacts said blood to pump the blood; and a balloon wrap, coupled to said stent and expandable by injection of fluid into a cavity thereof to fill said blood vessel.

2. The intravascular stent pump of claim 1, wherein said intravascular pump increases perfusion of blood through the vessel.

3. The intravascular stent pump of claim 1, wherein said intravascular pump assists in movement of volumes of blood through the blood vessel.

4. The intravascular stent pump of claim 1, wherein said blood flow is equal to or greater than a blood flow at the implant site before implantation.

5. The intravascular stent pump of claim 1, wherein said pump is configured and mounted at an appropriate position within a lumen of said stent enabling pumping an adequate blood flow through said lumen of the stent.

6. The stent pump of claim 1, wherein the intravascular stent is made of a material selected from a group consisting of Nitinol, stainless steel, shape memory alloy, and biocompatible plastic.

7. The intravascular stent pump of claim 1, wherein said blood vessel is an artery.

8. The stent pump of claim 1, wherein said blood vessel is a coronary artery.

9. The intravascular stent pump of claim 1, wherein said blood vessel is a periphery artery.

10. The intravascular stent pump of claim 1, wherein said blood vessel is a vein.

11. The intravascular stent pump of claim 1, wherein said blood vessel is a vein with chronic venous insufficiency.

12. The intravascular stent pump of claim 1, wherein said pump is a helical pump.

13. The intravascular stent pump of claim 1, further comprising a motor.

14. The intravascular stent pump of claim 1, wherein said pump is powered telemetrically.

15. The intravascular stent pump of claim 1, wherein said pump is powered by an implantable battery.

16. The intravascular stent pump of claim 1, wherein said pump is powered by electricity that is converted from body heat based on Peltier effects.

17. The intravascular stent pump of claim 1, wherein said pump is powered by electricity that is converted from mechanical motion of muscles based on a piezoelectric mechanism.

18. A pump as in claim 1, wherein said intravascular stent is substantially cylindrical and has a constant diameter throughout its entire length, and of a shape that can be inserted via a catheter.

19. A method for pumping fluid in a vessel of a human body, comprising:
a) positioning an endoluminal stent pump at a desired site of the vessel, wherein said stent pump comprises a stent and a pump mounted on said stent; and
b) pumping fluid using a cylinder that extends along a straight line central axis, having a cylindrical outer surface which has no blades thereon and has no grooves thereon, said pumping comprising rotating said cylindrical outer surface around said straight line central axis, and where the cylindrical surface with no blades thereon and no grooves thereon contacts the fluid to pump the fluid.

20. The method of claim 19, wherein said pump is mounted within a lumen of said stent, and wherein said pump allows an adequate fluid flow within the lumen of said stent.

21. The method of claim 20, wherein said pump is powered by an implantable battery.

22. The method of claim 19, wherein the step of positioning is carried out by providing a catheter having said stent pump releasably mounted on a distal end of the catheter, inserting the distal end of the catheter into the vessel, and advancing the catheter to position the stent pump at the desired site.

23. The method of claim 22, wherein the step of pumping fluid commences after the catheter is inserted into the vessel.

24. The method of claim 19, wherein the vessel is an artery.

25. The method of claim 19, wherein the vessel is a coronary artery.

26. The method of claim 19, wherein the vessel is a peripheral artery.

27. The method of claim 19, wherein the vessel is a vein.

28. The method of claim 24 or 27, wherein said pump is configured and adapted for allowing an adequate blood flow to prevent clotting within a lumen of said stent.

29. The method of claim 28, wherein said blood flow is equal to or greater than a blood flow at the desired site before implantation.

30. The method of claim 19, wherein the vessel is a vein with chronic venous insufficiency.

31. The method of claim 19, wherein the stent is balloon expandable.

32. The method of claim 19, wherein the stent is self-expanding.

33. The method of claim 19, wherein the stent is adapted to be expanded to fit the desired site of the vessel.

34. The method of claim 19, wherein the stent is made of a material selected from a group consisting of Nitinol, stainless steel, shape memory alloy, and biocompatible plastic.

35. The method of claim 19, wherein said pump is driven by a motor.

36. The method of claim 19, wherein said pump is powered by electricity that is converted from body heat based on Peltier effects.

37. The method of claim 19, wherein said pump is powered by electricity that is converted from mechanical motion of muscles based on piezoelectric mechanism.

38. The method of claim 19, wherein said pump is powered telemetrically.

39. A method as in claim 19, further comprising inflating a balloon wrap that is between said stent and a blood vessel, by injecting fluid into a cavity of the balloon wrap.

40. An intravascular miniature stent pump system for a blood vessel which carries blood, comprising:
an intravascular stent;
a bladeless pump mounted on said stent, the bladeless pump comprising an inner cylindrical element, which is rotatably mounted to rotate around a rotation axis, and where said inner cylindrical element has a substantially smooth outer surface which is substantially constant and where said cylindrical element extends along a straight line, and where said substantially smooth outer surface has a constant outer diameter cylindrical surface over an area of pumping and has no blades thereon and no grooves thereon in said area of pumping, and where said rotation axis is a central axis of said inner cylindrical element and where the substantially smooth outer surface of said inner cylindrical element contacts said blood and pumps said blood by contacting said blood; and
a chamber surface, wherein said chamber surface surrounds said inner element and has an inlet of fluid, at a first location along said rotation axis and an outlet for transmitting pumped fluid, at a different location along said rotation axis.

41. A pump system as in claim 40, further comprising a balloon wrap coupled to said stent, said balloon wrap having a capability of being inflated by injection of a fluid into a cavity of the balloon wrap.

42. An intravascular miniature stent pump system for a blood vessel with blood therein, said pump, comprising:
   an intravascular stent; and
   a bladeless pump mounted on said stent, said bladeless pump comprising a rotating constant diameter cylinder that extends along a straight line, which has no blades thereon and has no grooves thereon and wherein said constant diameter cylinder rotates around a central axis of the cylinder to produce a fluid flow in a direction substantially perpendicular to a direction of rotation using only non bladed and non-grooved smooth outer surfaces for pumping, where an outer surface of the constant diameter cylinder is a smooth cylindrical surface and where said outer surface of said smooth cylindrical surface contacts the blood to be pumped to pump said blood by contacting said blood.

43. The stent pump system of claim 42, further comprising a motor part which rotates said rotating constant diameter cylinder.

* * * * *